United States Patent [19]

Patten et al.

[11] Patent Number: 5,147,204
[45] Date of Patent: Sep. 15, 1992

[54] DENTAL MATERIAL CURING APPARATUS

[75] Inventors: Richard L. Patten, Minneapolis; Ronald A. Carlson, St. Croix Beach, both of Minn.

[73] Assignee: Minnesota Mining and Manufacturing Co., St. Paul, Minn.

[21] Appl. No.: 742,404

[22] Filed: Aug. 8, 1991

[51] Int. Cl.$^5$ .............................. A61C 1/00; A61C 3/00; G02B 6/14
[52] U.S. Cl. .................................... 433/229; 433/29; 250/504 H
[58] Field of Search ............... 433/29, 229, 109, 130; 250/504 R, 504 H

[56] References Cited

U.S. PATENT DOCUMENTS

| | | | |
|---|---|---|---|
| 2,326,773 | 8/1943 | Floyd | 176/1 |
| 3,509,629 | 5/1970 | Kidokoro | 433/130 |
| 3,712,984 | 1/1973 | Lienhard | 250/86 |
| 4,281,989 | 8/1981 | Glover et al. | 433/130 |
| 4,309,617 | 1/1982 | Long | 250/504 H |
| 4,385,344 | 5/1983 | Gonser | 362/32 |
| 4,450,139 | 5/1984 | Bussiere et al. | 422/186.3 |
| 4,460,337 | 7/1984 | Landgraf et al. | 433/29 |
| 4,614,498 | 9/1986 | Vaccaro | 433/126 |
| 4,623,795 | 11/1986 | Knopp et al. | 250/504 H |
| 4,818,231 | 4/1989 | Steiner et al. | 433/215 |
| 4,826,431 | 5/1989 | Fujimura et al. | 433/29 |
| 4,858,001 | 8/1989 | Milbank et al. | 358/98 |
| 4,872,837 | 10/1989 | Issalene et al. | 433/29 |
| 4,888,489 | 12/1989 | Bryan | 250/504 H |
| 4,948,215 | 8/1990 | Friedman | 350/96.1 |
| 4,975,058 | 12/1990 | Woodward | 433/126 |

OTHER PUBLICATIONS

Optilux Brochure, Demetron Research Corporation, copyright date unknown.
Demetron Brochure, Demetron Research Corporation, copyright date unknown.
Max Brochure, L. D. Caulk Division, Dentspy International, Inc., Copyright 1988.
Visilux II Brochure, 3M Company, 3M Deutschland GmbH, copyright date unknown.
Visilux 2 Brochure, 3M Company, copyright 1987.
Visilux 2 Field Service Handbook, 3M Company, pp. 2-1 to 2-5, 5-1 to 5-2, 6-1 to 6-5, copyright Sep. 1990.
Executor Brochure, Pro–Den Systems, Inc., copyright date unknown.
Executor, Poly-Fil Brochure, Pro–Den Systems, Inc., copyright date unknown.
Translux CL Brochure, Kulzer and Co. GmbH, copyright 1984.
Premierlite Brochure, Premier Dental Products Co., ESPE-Premier Sales Corp., copyright date unknown.
ESPE Elipar II Brochure, Fabrik Pharmazeutischer Praparate GmbH and Co. KG., copyright date unknown.
Teledyne Getz Brochure, Teledyne, Inc., copyright 1984.

Primary Examiner—Gene Mancene
Assistant Examiner—Cindy A. Cherichetti
Attorney, Agent, or Firm—Gary L. Griswold; Walter N. Kirn; James D. Christoff

[57] ABSTRACT

Light emitting apparatus for curing photocurable dental material includes a handpiece having a housing, a depending handle and a detachable light guide. The light guide is received in a head connected to the housing. Rotational movement of the head relative to the housing also rotatably moves the light guide so that the guide may be turned by the same hand of the user that is grasping the handle. Additionally, a pivotal connection between the housing and the handle permits limited pivotal adjustment of the angle of the housing relative to the handle for improved manipulation and user comfort. A base of the apparatus includes an upright pedestal that houses a device for determining the intensity of light provided by the light guide.

14 Claims, 3 Drawing Sheets

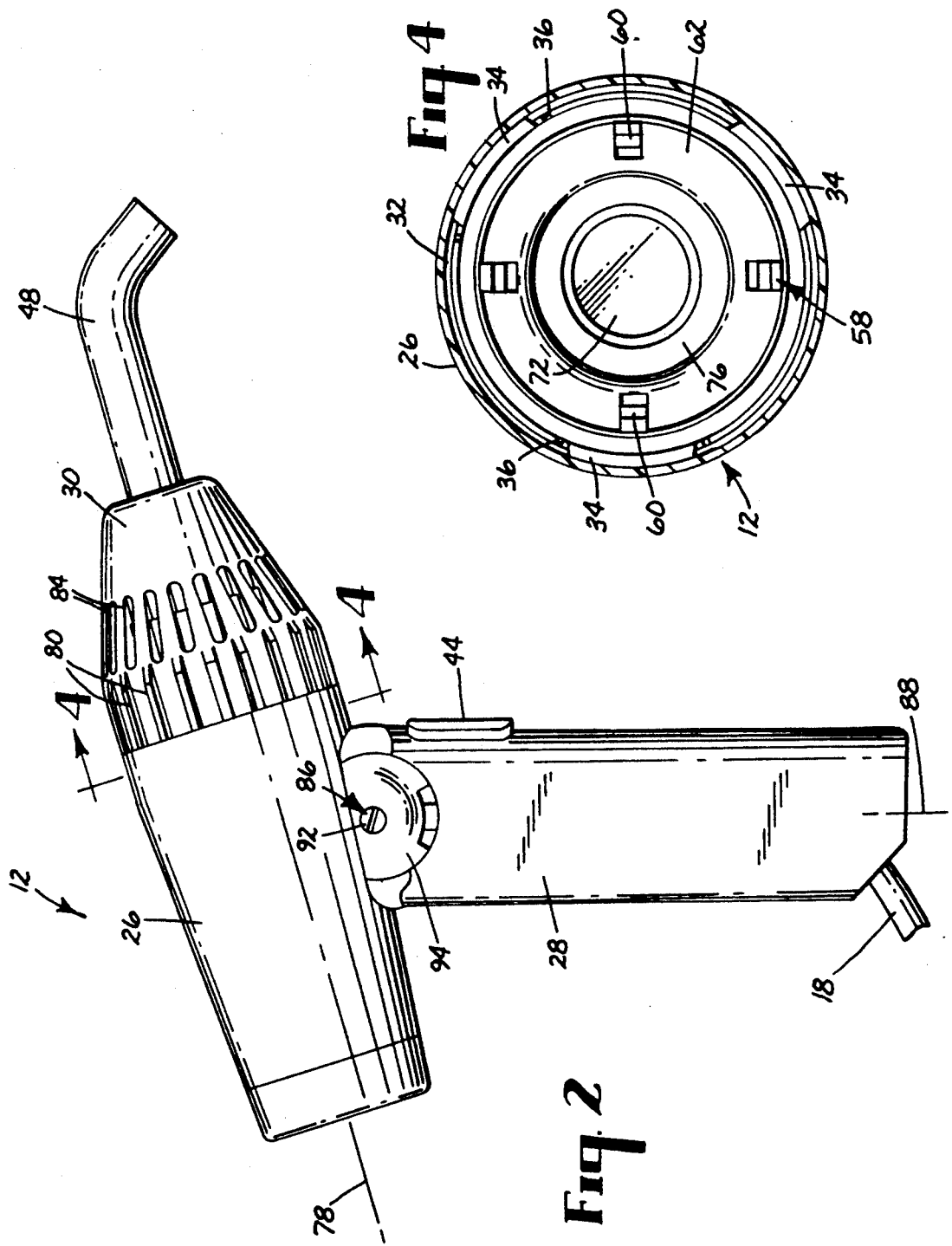

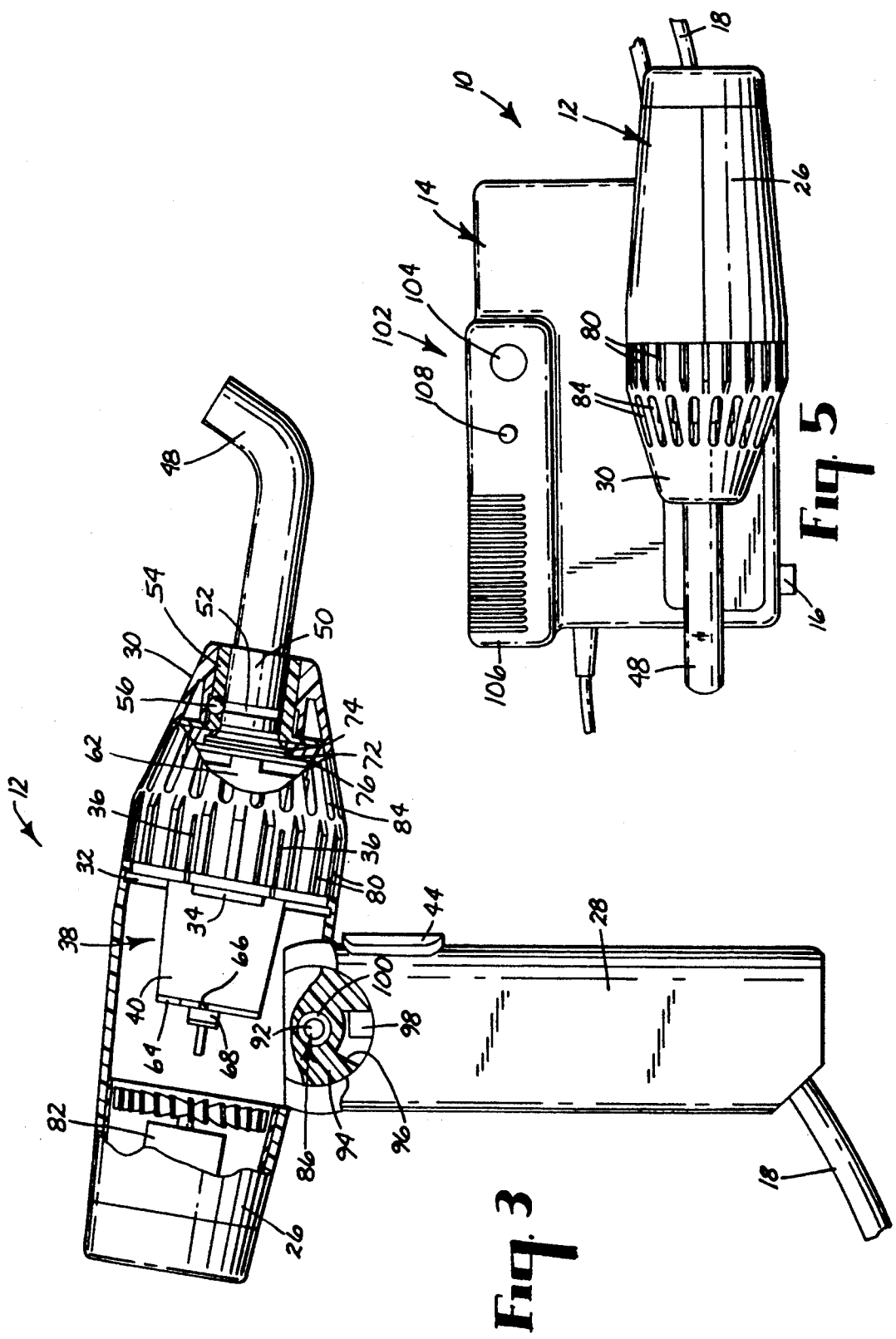

DENTAL MATERIAL CURING APPARATUS

BACKGROUND OF THE INVENTION

1. Field of the Invention

This invention broadly relates to light emitting apparatus for curing photocurable dental material.

2. Description of the Related Art

Certain materials used in the field of dentistry such as adhesives, sealants and restorative materials are cured upon exposure to a source of light. Preferably, the materials cure when exposed to light having a wavelength in the visible range.

Photocurable dental materials are a convenience to the dentist because the curing process can be initiated when desired. For example, a dental filling may be placed in a tooth cavity in contact with a photocurable dental adhesive and manipulated as needed until the dentist is satisfied that the filling is oriented in its proper position. A source of light next to the tooth cavity is then activated to initiate polymerization of the adhesive and securely fix the filling in place.

There is limited room in the oral cavity for a curing light. Consequently, conventional light curing apparatus often include an elongated, slender light guide such as a bundle of optical fibers having a free end that can be positioned close to the photocurable material in order to direct light to the material from a light source located outside the oral cavity. In addition, such light guides are often detachable from the light source so that the light guide can be sterilized between uses among different patients.

Certain known light curing apparatus have a light source located within a housing of a handpiece, and a detachable light guide of the apparatus is made of a rigid, fused bundle of glass optical fibers having an outer end portion that extends at an angle to the major portion of the light guide. The angled end portion facilitates directing the light to certain areas in the oral cavity that might otherwise be difficult to reach.

The rigid, angled light guide of some curing apparatus may be swiveled about its major, longitudinal axis in order to further enhance the maneuvering of the directed light. In order to turn the light guide relative to the housing of such apparatus, the light guide is normally turned by grasping the light guide with one hand and gripping a handle of the housing with the opposite hand. However, such a procedure may be cumbersome, and increases the likelihood of contamination of the light guide, thereby also increasing the patient's risk of infection.

In some instances, it is difficult to manipulate the light guide so that the outer end of the light guide is directly adjacent the photocurable material. Removing the light guide from the oral cavity, turning the light guide and then reinserting the light guide in the oral cavity is somewhat time consuming and may have to be repeated in order to arrive at a proper rotational position of the light guide relative to the housing. Even after a desired rotational position of the light guide is obtained, the resultant orientation of the handle may cause discomfort to the dentist.

SUMMARY OF THE INVENTION

The present invention relates to a light emitting apparatus for curing photocurable dental material, and comprises a housing and a handle for grasping by the user's hand. The handle depends from the housing and has a longitudinal axis. A head is connected to the housing and is movable in a rotational direction relative to the housing about a reference axis that is generally transverse to the longitudinal axis of the handle. A source of light is coupled to the housing, and a light guide is detachably connected to the head for communication with the source of light. The light guide is movable in a rotational direction about the reference axis with the head as the head is moved in a rotational direction relative to the housing. The head includes means engageable with the finger of the user's hand for moving the head and thereby the light guide in a rotational direction relative to the housing as the user's same hand grasps the handle.

The apparatus of the present invention is convenient to use and reduces the risk of infection because the head rather than the light guide is manipulated to turn the light guide and no direct contact of the dentist with the light guide is necessary for such manipulation. Further, the light guide need not be removed from the oral cavity during its rotational manipulation, enabling the dentist to observe the orientation of the light guide during its movement so that the desired orientation is attained in relatively short amount of time.

The invention also relates to a light emitting curing apparatus having a housing that is connected to a source of light and a handle depending from the housing. A pivotal connection provides selective pivotal movement of the handle relative to the housing.

Another aspect of the invention concerns a base with a receptacle for removably receiving a handpiece, and a device for determining the light intensity provided by the handpiece. The device includes a detector mounted on the base and an indicator for indicating when a predetermined intensity of light is detected by the detector.

BRIEF DESCRIPTION OF THE DRAWINGS

FIG. 2 is an enlarged rear side elevational view of the handpiece alone shown in FIG. 1 except that an upper housing of the handpiece is shown in an angular orientation (relative to a handle of the handpiece) that is different from the orientation of the housing shown in FIG. 1;

FIG. 3 is a view somewhat similar to FIG. 2 except that parts have been broken away in section, the angular orientation of the housing is different from its orientation shown in FIG. 2 and a rotational position of a light guide of the handpiece is different from its orientation shown in FIG. 2;

FIG. 4 is an enlarged sectional view taken along lines 4—4 of FIG. 2; and

FIG. 5 is a plan view of the apparatus illustrated in FIG. 1.

DETAILED DESCRIPTION OF THE PREFERRED EMBODIMENT

Figure 1:
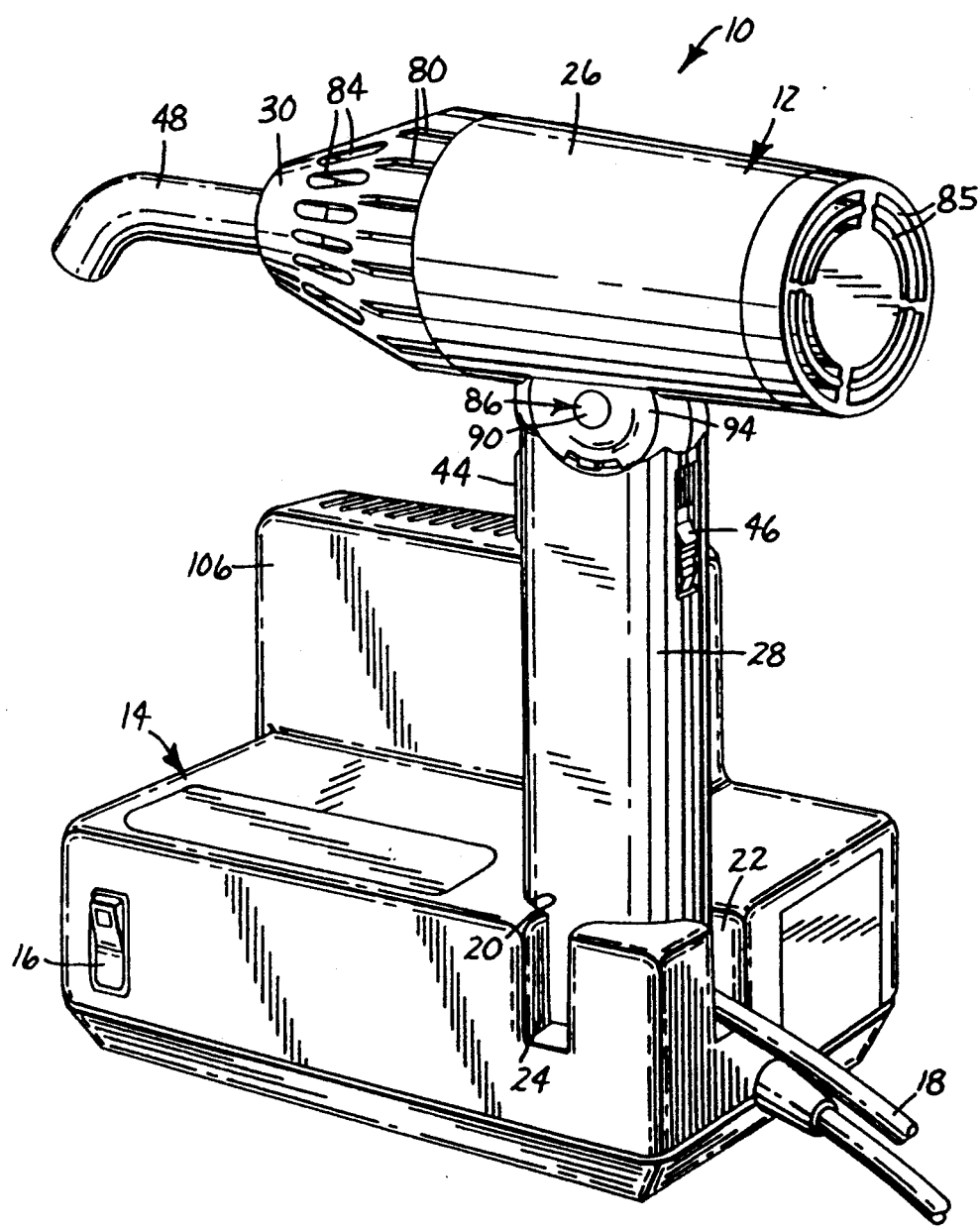
FIG. 1 is a top, front, right side perspective view of an apparatus of the present invention that includes a handpiece and a base.

A light emitting apparatus 10 for curing photocurable dental material is shown in FIGS. 1-4 and broadly includes a handpiece 12 and a power module base 14 (FIG. 1). The base 14 includes an on-off switch 16 as well as an internal power supply for rectifying and controlling the voltage of electrical current flowing from the base 14 to the handpiece 12 via a power cord 18.

A receptacle 20 formed in an upper surface of the base 14 removably receives the handpiece 12 as shown in FIG. 1 when the handpiece 12 is not in use. The receptacle 20 has a cross-sectional configuration adapted to receive the handpiece in either of two orientations. One such orientation is shown in FIG. 1, wherein the power cord 18 passes through a slot 22 of the receptacle 20. The other such orientation of the handpiece 12 is 90 degrees from its orientation shown in FIG. 1 about a vertical axis, and in such an orientation the power cord 18 passes through a second slot 24 of the receptacle 20.

The handpiece 12 includes a hollow, somewhat frustoconical housing 26 and an elongated handle 28 that depends from the housing 26 to form a pistol-type grip. A front head 30 is rotatably connected to the housing 26 and includes a rear, somewhat cylindrical portion and a front, somewhat frustoconical portion.

An inner surface of the front of the housing 26 is circumscribed by a groove 32 that is shown in FIGS. 3 and 4. The head 30 includes three flanges 34 that slide along the groove 32 as the head 30 is rotatably moved relative to the housing 26 about central, longitudinal axes of the head 30 and the housing 26. The head 30 is made of a synthetic resinous material and has two pair of rear slots 36 (one pair of which is shown in FIG. 3) that straddle two of the three flanges 34. The head 30 can be disassembled from the housing 26 to change an internal lamp 40 by pressing inwardly on the somewhat flexible flanges 34 straddled by the slots 36 in order to enable the flanges 34 to clear the front inner edge of the housing 26 and be moved away from respective positions in the groove 32.

A source of light 38 (FIG. 3) carried in the housing 26 includes the tungsten-halogen lamp 40 within a concave reflector. The lamp 40 is activated by finger pressure on a push-button switch 44 mounted on a front, upper region of the handle 28. A slide switch 46 (FIG. 1) located on the rear portion of the handle 28 provides a choice of time durations (such as 10, 20, 40 and 60 second periods) for activation of the lamp 40.

A rigid light guide 48 is made of a bundle of optical fibers that are fused together and is detachably connected to the head 30 for communication with the source of light 38. The rearward end of the light guide 48 has a metallic, somewhat cylindrical collar 50 formed with a peripheral channel 52 (FIG. 3).

The head 30 includes a cylindrical, tubular insert 54 that provides a receptacle for receiving the collar 50 of the light guide 48. A side hole formed in the insert 54 is tapered for retaining a small steel ball 56 in place. The ball 56 is resiliently urged inwardly in a radial direction toward the center of the insert 54 by a tab-like portion of the head 30 that is next to the hole of the insert 54. The ball 56 engages the channel 52 to releasably retain the light guide 48 in place as shown in the drawings, and may be moved slightly in a radially outwardly direction against the pressure of the tab-like portion to allow the light guide 48 to be detached from the head 30 when desired.

The head 30 houses a spider-like support 58 having four legs 60 that pass through holes of a baffle 62 as shown in FIG. 4. The rear ends of the legs 60 have tapered inner surfaces that engage the outer, front edge of the reflector.

As illustrated in FIG. 3, the source of light 38 includes a mount having a pair of outer arms 64 (only one shown). Each arm 64 has a slot 66 that rides a limited distance along a rail that is integrally connected to the interior of the housing and that extends in a front-to-back orientation parallel to a reference axis 78 (FIG. 2). A leaf spring 68 is connected to the source of light 38 and has outer arms that press against inner flanges of the housing 26 in order to urge the source of light 38 toward the head 30. The spring 68 urges the front edge of the reflector toward the tapered inner surfaces of the support legs 60, and the tapered surfaces cause the lamp 40 and the reflector to be aligned with the central axis of the support 58 and thereby with the central axis of the head 30 and the light guide 48.

The support 58 surrounds a blue-pass filter 72 and a heat filter 74 which are shown in FIG. 3. The filters 72, 74 are retained against the support 58 by an annular spacer 76 that abuts the front end of the baffle 62.

Typically, the photochemical reaction in many photocurable dental materials is initiated by high intensity blue light having a wave length of 420-500 nanometers. Since the lamp 40 produces the entire visible light spectrum as well as some nonvisible radiation, the reflector is coated to generally reflect only visible light, and the filters 72, 74 are selected to substantially block non-visible radiation and visible light other than blue light in the range of 420-500 nanometers. Further, the reflector is shaped to focus reflected light emitted from the lamp 40 to the rear planar end of the light guide 48 when the light guide 48 is received in the head 30.

The head 30 and the light guide 48 are together rotatably movable relative to the housing 26 without limit in either direction about the reference axis 78 (FIG. 2) that is coincident with the central, longitudinal axes of the housing 26, the head 30 and the major extent of the light guide 48. As the head 30 is swiveled relative to the housing 26, the flanges 34 ride along the groove 32. The inward pressure of the ball 56 against the collar 50 insures that the light guide 48 turns simultaneously with rotational movement of the head 30.

As illustrated in FIGS. 1-3, an outer surface of the head 30 is provided with a spaced series of peripheral projections or tabs 80 that radiate outwardly from the axis 78 and extend in a front-to-back direction. The tabs 80 provide a manual manipulative control engageable with a finger of the user's hand for single-handedly moving the head 30 and thereby the light guide 48 in a rotational direction relative to the housing 26 from one operating position to another as the remaining fingers of the user's same hand grasp the handle 28. Alternative means for rotatably moving the head 30 could also be used such as a series of recesses or openings (see, e.g., openings 84) or a knurled surface for frictional engagement with the user's finger.

A blower 82 is mounted in a rear portion of the housing 26 for cooling the lamp 40. The blower 82 is activated by control circuitry within the handle 28 for operation beginning a few seconds after the lamp 40 is energized, and terminating in about two minutes from the time that the lamp 40 is de-energized unless the lamp is re-energized within such period. In operation, the blower 82 draws in air through a series of openings 84 located in the head 30 for circulation around the lamp 40 and discharge through a series of rear apertures 85 (see FIG. 1) formed in the housing 26.

Advantageously, a pivotal connection 86 couples the handle 28 to the housing 26 for selective pivotal movement of the handle 28 relative to the housing 26 about an axis that is generally normal to the axis 78 and a longitudinal axis 88 (FIG. 2) of the handle 28. The pivotal connection 86 includes a bolt 90 (FIG. 1) connected to a nut 92 having a head (FIGS. 2-3). The assembly of the bolt 90 and nut 92 passes through a hole in the upper portion of the handle 28, as well as holes formed in depending, spaced apart ears 94 that straddle the upper portion of the handle 28.

The ears 94 each have an inwardly, inverted, somewhat U-shaped recess 96 (FIG. 3) that surrounds a protruding stop 98 formed on respective sides of the handle 28. Two rubber O-rings 100 (one of which is shown in FIG. 3) surround the assembly of the bolt 90 and the nut 92 and are positioned in recesses formed in the handle 26. The O-rings 100 are in frictional contact with the ears 94 to ensure secure positionings of the handle 28 relative to the housing 26 so that intentional manual pressure is required to change the orientation of the handle 28 relative to the housing 26.

The recesses 96 and the stops 98 define the extent of pivotal motion of the housing 26 relative to the handle 28 about the connection 86. In FIG. 3, the housing 26 is shown in a fully tipped-down orientation wherein the axis 78 is oriented about 80 degrees from the axis 88. Further movement in a downward direction is hindered because the front portion of the recess 96 is in abutting contact with the front portion of the stop 98. In FIG. 2, the head 30 is shown as pivoted about the connection 86 to a fully upward orientation wherein the axis 78 is about 105 degrees relative to the axis 88. Further upward movement of the housing 26 is hindered because of the mutual engagement of the rear portions of the recess 96 and the stop 98.

Advantageously, either of the swivel adjustments of the handpiece 12 can be made with the same hand of the user that is grasping the handle 28. For example, to tilt the housing 26 relative to the handle 28 from the position shown in FIG. 1 to either of the positions shown in FIGS. 2 or 3 or, for that matter, to any position between the positions shown in FIGS. 2 and 3, the user need merely press upwardly on the front or rear portion of the housing 26 with the thumb or forefinger while the remaining fingers of the same hand retain a grip on the handle 28. Also, rotational movement of the light guide 48 may be made with the forefinger of such hand by urging of the tabs 80 in a circular direction about the axis 78.

As depicted in FIG. 5, the apparatus 10 includes a device 102 in the nature of a threshold meter that selectively measures the light output of the source of light 38. The device 102 includes a photocell detector 104 that is mounted atop an upright pedestal 106 of the base 14. Additionally, a green LED indicator 108 is located next to the detector 104 on the pedestal 106.

The device 102 includes a logic circuit in the base 14 that is electrically coupled to the detector 104 and the indicator 108 as well as the power supply in the base 14 that supplies current to the handpiece 12. The logic circuit includes a comparator that compares the voltage provided by the detector 104 with a reference voltage.

In use, the outer end of the light guide 48 is held next to the detector 104 while the lamp 40 is activated. If the voltage provided by the detector 104 is at least as great as the reference voltage, the comparator energizes the indicator 108. As a result, the indicator 108 provides an illuminated signal to the user that sufficient light is available to satisfactorily cure photocurable dental materials whenever the intensity of light emitted by the light guide is at least as great as a minimum threshold value. In practice, the indicator 108 is illuminated whenever the light output sensed by the detector 104 is greater than 170 milliwatts.

Although not shown, the apparatus 10 includes a beeper that provides an audible signal when the lamp 40 is activated. The beeper also provides a signal when the lamp 40 is deactivated at the end of its selected time period of energization.

We claim:

1. Light emitting apparatus for curing photocurable dental material comprising:
    a housing:
    a handle for grasping by a user's hand, said handle depending from said housing and having a longitudinal axis;
    a head connected to said housing and movable in a rotational direction relative to said housing about a reference axis that is generally transverse to said longitudinal axis of said handle;
    a source of light coupled to said housing; and
    a light guide detachably connected to said head for communication with said source of light and movable in a rotational direction about said reference axis with said head as said head is moved in a rotational direction relative to said housing,
    said head including means engageable with a finger of the user's hand for single-handedly moving said head and thereby said light guide in a rotational direction relative to said housing from one operating position to another as the user's same hand grasps said handle.

2. The apparatus of claim 1, wherein said head includes an outer surface, and wherein said means includes a series of projections on said outer surface.

3. The apparatus of claim 2, wherein said projections comprise tabs extending outwardly from said reference axis.

4. The apparatus of claim 1, wherein said head includes an outer surface, and wherein said means comprises a series of openings in said outer surface.

5. The apparatus of claim 1, wherein said light guide has a generally cylindrical end and wherein said head includes a generally cylindrical receptacle for reception of said end.

6. The apparatus of claim 5, wherein said end of said light guide has a diameter that is approximately the same as the inner diameter of said receptacle to provide a relatively close tolerance fit between said end and said receptacle for facilitating movement of said light guide with said head in a rotational direction as said head is moved in a rotational direction.

7. The apparatus of claim 1; and including a pivotal connection coupling said handle to said housing for selective pivotal movement of said handle relative to said housing about an axis that is generally normal to said reference axis and to said longitudinal axis of said handle.

8. Light emitting apparatus for curing photocurable dental material comprising:
    a housing;
    a source of light connected to said housing;
    a light guide connected to said housing for communication with said source of light, said light guide extending in a direction away from said housing along a reference axis;
    a handle depending from said housing and having a longitudinal axis generally transverse to said axis; and a pivotal connection coupling said handle to said housing for selective pivotal movement of said handle relative to said housing about an axis that is generally normal to said reference axis and to said longitudinal axis.

9. The apparatus of claim 8, wherein said housing includes a pair of depending ears that straddle said handle, and wherein said pivotal connection extends through said ears.

10. The apparatus of claim 9, wherein said ears include means for limiting the pivotal movement of said handle relative to said housing.

11. Light emitting apparatus for curing photocurable dental material comprising:

a handpiece including a source of light;

a base including a receptacle for removably receiving said handpiece; and a device for determining the light intensity of said source of light, said device including a detector mounted on said base and an indicator for indicating when a predetermined quantity of light intensity is detected by said detector.

12. The apparatus of claim 11, wherein said base includes a power supply, and wherein said handpiece and said device are each electrically coupled to said power supply.

13. The apparatus of claim 11, wherein said base includes an upright pedestal, and wherein said detector is mounted on said pedestal at a location above said receptacle.

14. The apparatus of claim 11, wherein said indicator includes means for providing an illuminated signal.

* * * * *